United States Patent
Grandjean et al.

(10) Patent No.: US 10,399,925 B2
(45) Date of Patent: Sep. 3, 2019

(54) BETA-HYDROXYLATED TERTIARY DIAMINES, A PROCESS FOR THEIR SYNTHESIS AND THEIR USE FOR ELIMINATING ACID COMPOUNDS A GASEOUS EFFLUENT

(71) Applicant: IFP Energies nouvelles, Rueil-Malmaison (FR)

(72) Inventors: Julien Grandjean, Lyons (FR); Bruno Delfort, Paris (FR); Dominique Le Pennec, Orgerus (FR); Thierry Huard, Saint Symphorien d'Ozon (FR); Aurelie Wender, Rueil-Malmaison (FR); Armelle Nigon, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 15/972,275

(22) Filed: May 7, 2018

(65) Prior Publication Data

US 2018/0251421 A1     Sep. 6, 2018

Related U.S. Application Data

(62) Division of application No. 15/311,232, filed as application No. PCT/EP2015/060516 on May 12, 2015, now abandoned.

(30) Foreign Application Priority Data

May 16, 2014 (FR) ...................................... 14 54371

(51) Int. Cl.
B01D 53/14 (2006.01)
B01D 53/52 (2006.01)
(Continued)

(52) U.S. Cl.
CPC ........ *C07C 215/18* (2013.01); *B01D 53/1456* (2013.01); *B01D 53/1462* (2013.01);
(Continued)

(58) Field of Classification Search
None
See application file for complete search history.

(56) References Cited

U.S. PATENT DOCUMENTS

| 3,867,454 A | 2/1975 | Diana et al. |
| 4,405,582 A | 9/1983 | Stogryn et al. |

(Continued)

FOREIGN PATENT DOCUMENTS

| DE | 23 20 189 A1 | 11/1974 |
| FR | 2934172 A1 | 1/2010 |
| WO | 2013060944 A1 | 5/2013 |

OTHER PUBLICATIONS

International Search Report for PCT/EP2015/060516 dated Aug. 4, 2015; English translation submitted herewith (7 Pages).

*Primary Examiner* — Daniel Berns
(74) *Attorney, Agent, or Firm* — Fitch, Even, Tabin & Flannery, LLP

(57) ABSTRACT

The invention relates to novel nitrogen compounds belonging to the family of tertiary diamines of general formula (I) below, wherein R is an alkanediyl radical —$(CH_2)_n$- with n=2, 3, 4, 5 or 6.

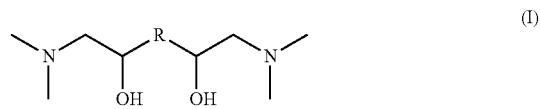

(I)

The compound according to the invention is for example N,N,N',N'-(tetramethyl)-1,6-diamino-2,5-hexanediol or (Continued)

N,N,N',N'-(tetramethyl)-1,8-diamino-2,7-octanediol. The invention also relates to the method for preparing them and to their use for removing acid compounds contained in a gaseous effluent.

13 Claims, 1 Drawing Sheet

(51) Int. Cl.
*B01D 53/62* (2006.01)
*C07C 215/18* (2006.01)
*C07C 213/04* (2006.01)
*C10K 1/00* (2006.01)
*C10K 1/14* (2006.01)
*C10L 3/10* (2006.01)

(52) U.S. Cl.
CPC ..... *B01D 53/1468* (2013.01); *B01D 53/1493* (2013.01); *C07C 213/04* (2013.01); *C10K 1/003* (2013.01); *C10K 1/004* (2013.01); *C10K 1/005* (2013.01); *C10K 1/143* (2013.01); *C10L 3/102* (2013.01); *C10L 3/103* (2013.01); *C10L 3/104* (2013.01); *B01D 2252/103* (2013.01); *B01D 2252/2023* (2013.01); *B01D 2252/2041* (2013.01); *B01D 2252/20431* (2013.01); *B01D 2252/20489* (2013.01); *B01D 2252/504* (2013.01); *B01D 2257/304* (2013.01); *B01D 2257/306* (2013.01); *B01D 2257/308* (2013.01); *B01D 2257/504* (2013.01); *B01D 2258/0233* (2013.01); *B01D 2258/0283* (2013.01); *B01D 2258/05* (2013.01); *C10L 2290/541* (2013.01); *Y02P 20/152* (2015.11)

(56) References Cited

U.S. PATENT DOCUMENTS

| 4,405,583 | A | 9/1983 | Stogryn et al. |
| 5,277,885 | A | 1/1994 | Peytavy et al. |
| 6,852,144 | B1 | 2/2005 | Wagner et al. |
| 2010/0105551 | A1 | 4/2010 | Kim et al. |
| 2011/0185901 | A1 | 8/2011 | Jacquin et al. |
| 2013/0243677 | A1 | 9/2013 | Siskin et al. |

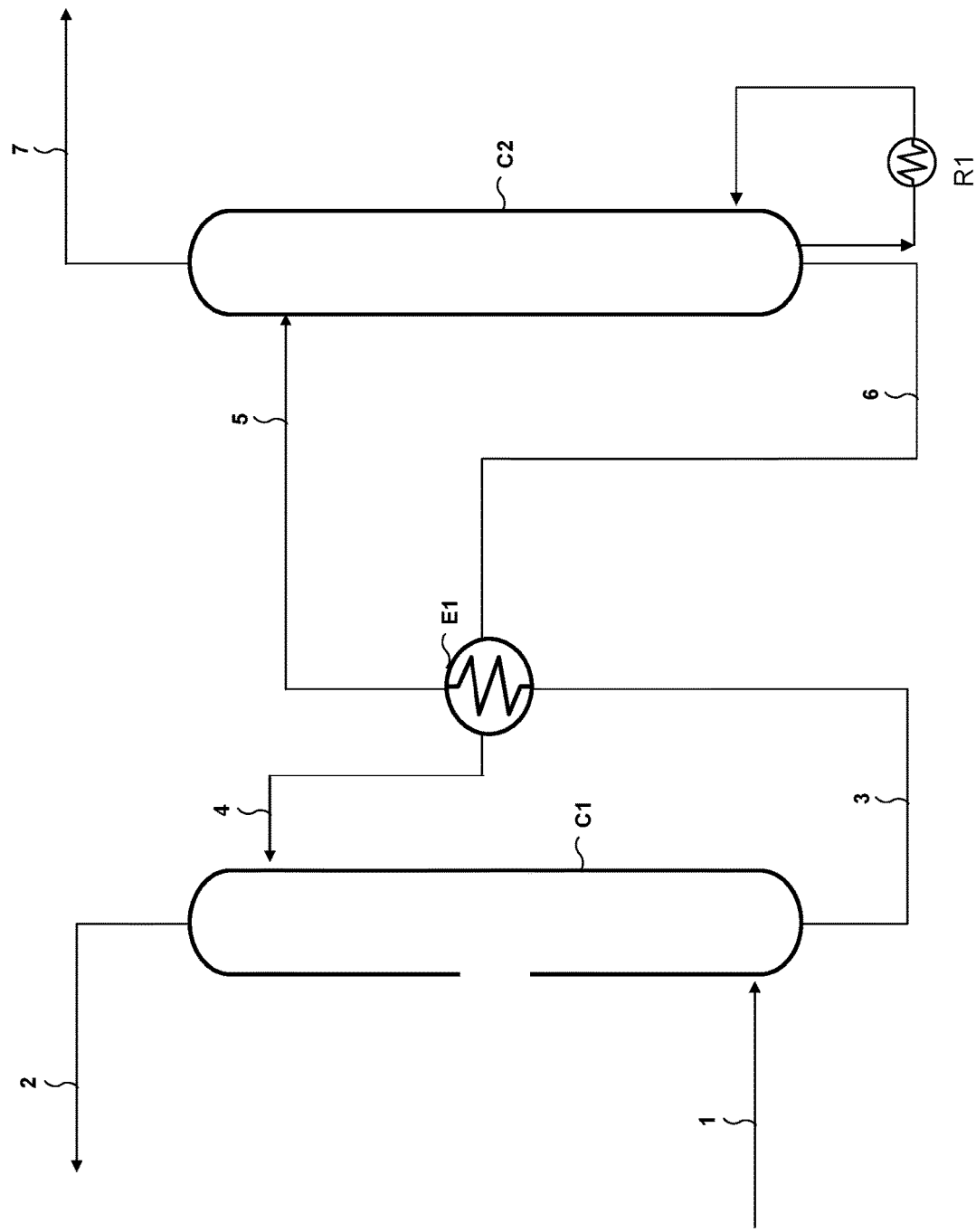

BETA-HYDROXYLATED TERTIARY DIAMINES, A PROCESS FOR THEIR SYNTHESIS AND THEIR USE FOR ELIMINATING ACID COMPOUNDS A GASEOUS EFFLUENT

CROSS-REFERENCE TO RELATED APPLICATIONS

This application is a divisional application of U.S. application Ser. No. 15/311,232 filed Nov. 15, 2016, which is a 371 of International Application No. PCT/EP2015/060516, filed May 12, 2015, which claims priority to FR 14/54.371, filed May 16, 2014, the contents of each of which are incorporated herein by reference.

FIELD OF THE INVENTION

The present invention relates to novel nitrogen compounds belonging to the family of beta-hydroxylated tertiary diamines. The invention also relates to the synthesis method of said compounds and to their use in a method of deacidizing a gaseous effluent.

BACKGROUND OF THE INVENTION

Tertiary amines, notably some tertiary diamines, are of interest for various applications. They can for example be used as catalysts in the preparation of polyurethanes, as quaternary ammonium salt precursors or as bases for acid gas deacidizing.

Tertiary amines can be utilized in acid gas deacidizing methods using an aqueous solution comprising such amines for removing acid compounds, notably carbon dioxide ($CO_2$), hydrogen sulfide ($H_2S$), carbon oxysulfide (COS), carbon disulfide ($CS_2$), sulfur dioxide ($SO_2$) and mercaptans (RSH) such as methylmercaptan ($CH_3SH$), ethylmercaptan ($CH_3CH_2SH$) and propylmercaptan ($CH_3CH_2CH_2SH$), present in a gas. The gas is deacidized by being contacted with the absorbent solution, then the absorbent solution is thermally regenerated.

These acid gas deacidizing methods are also commonly known as "solvent scrubbing", using a solvent referred to as "chemical", as opposed to the use of a solvent referred to as "physical" for absorption that is not based on chemical reactions.

A chemical solvent corresponds to an aqueous solution comprising a reactant that reacts selectively with the acid compounds ($H_2S$, $CO_2$, COS, $CS_2$, etc.) present in the treated gas so as to form salts, without reacting with the other non-acid compounds in the gas. After contacting with the solvent, the treated gas is depleted in acid compounds that are selectively transferred as salts into the solvent. The chemical reactions are reversible, which allows the acid compound-laden solvent to be subsequently deacidized, for example under the action of heat, so as to release on the one hand the acid compounds in form of gas that can then be stored, converted or used for various applications, and on the other hand to regenerate the solvent that goes back to its initial state and can thus be used again for a new reaction stage with the acid gas to be treated. The reaction stage of the solvent with the acid gas is commonly referred to as absorption stage, and the stage where the solvent is deacidized is referred to as solvent regeneration stage.

In general, the performances of the separation of acid compounds from the gas in this context mainly depend on the nature of the reversible reaction selected. Conventional acid gas deacidizing methods are generally referred to as "amine methods", i.e. based on the reactions of the acid compounds with amines in solution. These reactions are part of the overall framework of acid-base reactions. $H_2S$, $CO_2$ or COS are for example acid compounds, notably in the presence of water, whereas amines are basic compounds. The reaction mechanisms and the nature of the salts obtained generally depend on the structure of the amines used.

For example, document U.S. Pat. No. 6,852,144 describes a method of removing acid compounds from hydrocarbons using a water-N-methyldiethanolamine or water-triethanolamine absorbent solution with a high proportion of a compound belonging to the following group: piperazine and/or methylpiperazine and/or morpholine.

The performances of acid gas deacidizing methods using amine scrubbing directly depend on the nature of the amine(s) present in the solvent. These amines can be primary, secondary or tertiary. They can have one or more equivalent or different amine functions per molecule.

In order to improve the performances of deacidizing methods, increasingly efficient amines are continuously sought.

One limitation of the absorbent solutions commonly used in deacidizing applications is insufficient $H_2S$ absorption selectivity over $CO_2$. Indeed, in some natural gas deacidizing cases, selective $H_2S$ removal is sought by limiting to the maximum $CO_2$ absorption. This constraint is particularly important for gases to be treated already having a $CO_2$ content that is less than or equal to the desired specification. A maximum $H_2S$ absorption capacity is then sought with maximum $H_2S$ absorption selectivity over $CO_2$. This selectivity allows to maximize the amount of treated gas and to recover an acid gas at the regenerator outlet having the highest $H_2S$ concentration possible, which limits the size of the sulfur chain units downstream from the treatment and guarantees better operation. In some cases, an $H_2S$ enrichment unit is necessary for concentrating the acid gas in $H_2S$. In this case, the most selective amine is also sought. Tertiary amines such as N-methyldiethanolamine or hindered secondary amines exhibiting slow reaction kinetics with $CO_2$ are commonly used, but they have limited selectivities at high $H_2S$ loadings.

It is well known to the person skilled in the art that tertiary amines or secondary amines with severe steric hindrance have slower $CO_2$ capture kinetics than less hindered primary or secondary amines. On the other hand, tertiary or secondary amines with severe steric hindrance have instantaneous $H_2S$ capture kinetics, which allows to achieve selective $H_2S$ removal based on distinct kinetic performances.

Various documents propose using hindered tertiary or secondary amines, in particular tertiary diamines in solution for deacidizing acid gases.

Among the applications of tertiary or secondary amines with severe steric hindrance, U.S. Pat. No. 4,405,582 describes a method for selective absorption of sulfur-containing gases with an absorbent containing a diaminoether at least one amine function of which is tertiary and whose other amine function is tertiary or secondary with severe steric hindrance, the nitrogen atom being in the latter case linked to either at least one tertiary carbon or to two secondary carbon atoms. The two amine functions and the carbons of the main chain can be substituted by alkyl or hydroxyalkyl radicals.

U.S. Pat. No. 4,405,583 also describes a method for selective removal of $H_2S$ in gases containing $H_2S$ and $CO_2$ with an absorbent containing a diaminoether whose two secondary amine functions exhibit severe steric hindrance as defined above. The substituents of the amine functions and of the carbons of the main chain can be substituted by alkyl and hydroxyalkyl radicals.

Patent FR-2,934,172 describes the use of an absorbent solution based on a tertiary diamine in an acid compound removal method advantageously applied to the treatment of natural gas and combustion fumes, said amine being N,N,N',N'-tetramethyl-1,6-hexanediamine.

Another limitation of the absorbent solutions commonly used in total deacidizing applications is too slow $CO_2$ or COS capture kinetics. In cases where the desired $CO_2$ or COS specifications level is very high, the fastest possible reaction kinetics is sought so as to reduce the height of the absorption column. Indeed, this equipment under pressure represents a significant part of the investment costs of the process.

Whether seeking maximum $CO_2$ and COS capture kinetics in a total deacidizing application or minimum $CO_2$ capture kinetics in a selective application, it is always desirable to use an absorbent solution having the highest cyclic capacity possible. This cyclic capacity, denoted by $\Delta\alpha$, corresponds to the loading difference ($\alpha$ designates the number of moles of absorbed acid compounds $n_{acid\ gas}$ per kilogram of absorbent solution) between the absorbent solution discharged from the bottom of the absorption column and the absorbent solution fed to said column. Indeed, the higher the cyclic capacity of the absorbent solution, the lower the absorbent solution flow rate required for deacidizing the gas to be treated. In gas treatment methods, reduction of the absorbent solution flow rate also has a great impact on the reduction of investments, notably as regards absorption column sizing.

Another essential aspect of gas or industrial fumes treatment operations using a solvent remains the regeneration of the separation agent. Regeneration through expansion and/or distillation and/or entrainment by a vaporized gas referred to as "stripping gas" is generally considered depending on the absorption type (physical and/or chemical). The energy consumption required for solvent regeneration can be very high, which is in particular the case when the partial pressure of acid gases is low, and it can represent a considerable operating cost for the $CO_2$ capture process.

It is well known to the person skilled in the art that the energy required for regeneration by distillation of an amine solution can be divided into three different items: the energy required for heating the absorbent solution between the top and the bottom of the regenerator, the energy required for lowering the acid gas partial pressure in the regenerator by vaporization of a stripping gas, and the enthalpy required for breaking the chemical bond between the amine and the $CO_2$.

These first two items are proportional to the absorbent solution flows to be circulated in the plant in order to achieve a given specification. In order to decrease the energy consumption linked with the regeneration of the solvent, the cyclic capacity of the solvent is therefore once again preferably maximized. Indeed, the higher the cyclic capacity of the absorbent solution, the lower the absorbent solution flow rate required for deacidizing the gas to be treated.

There is therefore a need, in the field of gas deacidizing, for compounds that are good candidates for acid compounds removal from a gaseous effluent, notably, but not exclusively, selective removal of $H_2S$ over $CO_2$, and that allow operation at lower operating costs (including the regeneration energy) and investment costs (including the cost of the absorption column).

DESCRIPTION OF THE INVENTION

The inventors have discovered novel nitrogen compounds belonging to the family of beta-hydroxylated tertiary diamines which can be advantageously used in the field of gas deacidizing.

The inventors have found that tertiary or secondary diamines with severe steric hindrance are not equivalent in terms of performance for use in absorbent solution formulations for acid gas treatment in an industrial process.

The novel nitrogen compounds according to the invention are particular tertiary diamines whose main chain, i.e. the chain linking the two tertiary amine functions, is a hydrocarbon chain substituted by two hydroxyl groups, each hydroxyl group being carried by a carbon atom at nitrogen beta position. The term beta-hydroxylated tertiary diamine is used in the present invention in reference to the position of a hydroxyl group with respect to an amine function as described.

SUMMARY OF THE INVENTION

According to a first aspect, the invention relates to a nitrogen compound belonging to the family of tertiary diamines meeting general formula (I) as follows:

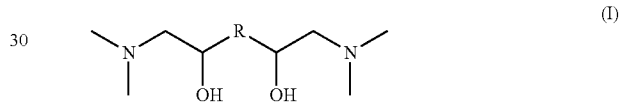

wherein R is an alkanediyl radical —$(CH_2)n$- with n=2, 3, 4, 5 or 6.

Preferably, the nitrogen compound according to the invention is N,N,N',N'-(tetramethyl)-1,6-diamino-2,5-hexanediol meeting the formula as follows, with n equal to 2 and R being an ethylidene radical:

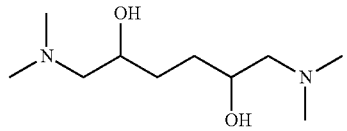

Preferably, the nitrogen compound according to the invention is N,N,N',N'-(tetramethyl)-1,8-diamino-2,7-octanediol meeting the formula as follows, with n equal to 4 and R being a butylidene radical:

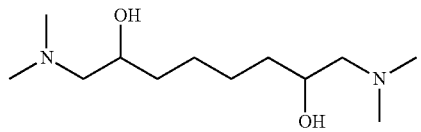

According to a second aspect, the invention relates to a synthesis method of a nitrogen compound according to general formula (I) comprising the following reactions:

a first reaction of epoxidation of an alpha-omega-diene to achieve epoxidation of each one of the alkene functions of the alpha-omega-diene to oxirane functions so as to produce a diepoxyalkane, a second reaction of addition of two moles of dimethylamine and one molecule of the diepoxyalkane so as to produce the nitrogen compound according to general formula (I).

According to one embodiment, the first reaction is an epoxidation reaction of 1,5-hexadiene to produce 1,2,5,6-diepoxyhexane, and the second reaction is an addition reaction of two moles of dimethylamine and one molecule of 1,2,5,6-diepoxyhexane to produce N,N,N',N'-(tetramethyl)-1,6-diamino-2,5-hexanediol.

According to an embodiment, the first reaction is an epoxidation reaction of 1,7-octadiene to produce 1,2,7,8-diepoxyoctane, and the second reaction is an addition reaction of two moles of dimethylamine and one molecule of 1,2,7,8-diepoxyoctane to produce N,N,N',N'-(tetramethyl)-1,8-diamino-2,7-octanediol.

Preferably, the first epoxidation reaction consists in reacting the alpha-omega-diene with a peracid or a peroxide or a hydroperoxide or oxygen associated with a suitable catalytic system, and said peracid can be generated in situ by reaction between a carboxylic acid and a hydrogen peroxide.

Advantageously, the second addition reaction is carried out in the presence of excess dimethylamine, preferably more than two moles.

According to an embodiment, the first epoxidation reaction and the second addition reaction are carried out in two successive stages.

According to a third aspect, the invention relates to a method of removing acid compounds contained in a gaseous effluent wherein an acid compound absorption stage is carried out by contacting the gaseous effluent with an absorbent solution comprising water and a nitrogen compound according to the invention or likely to be obtained by a synthesis method according to the invention.

Preferably, the absorbent solution comprises between 5 wt. % and 95 wt. % of said nitrogen compound, preferably between 10 wt. % and 90 wt. % of said nitrogen compound, and between 5 wt. % and 95 wt. % of water, preferably between 10 wt. % and 90 wt. % of water.

Furthermore, the absorbent solution can comprise between 5 wt. % and 95 wt. % of at least one additional amine, said additional amine being either a tertiary amine or a secondary amine having two secondary carbons at nitrogen alpha position or at least one tertiary carbon at nitrogen alpha position.

Said additional amine can be a tertiary amine selected from among the group made up of:
N-methyldiethanolamine,
triethanolamine,
diethylmonoethanolamine,
dimethylmonoethanolamine, and
ethyldiethanolamine.

The absorbent solution can also comprise a non-zero amount, less than 30 wt. %, of at least one additional amine such as a primary amine or a secondary amine.

Said additional primary or secondary amine can be selected from among the group made up of:
monoethanolamine,
diethanolamine,
N-butylethanolamine,
aminoethylethanolamine,
diglycolamine,
piperazine,
1-methylpiperazine,
2-methylpiperazine,
homopiperazine,
N-(2-hydroxyethyl)piperazine,
N-(2-aminoethyl)piperazine,
morpholine,
3-(methylamino)propylamine,
1,6-hexanediamine,
N,N-dimethyl-1,6-hexanediamine,
N,N'-dimethyl-1,6-hexanediamine,
N-methyl-1,6-hexane-diamine, and
N,N',N'-trimethyl-1,6-hexanediamine.

The absorbent solution can furthermore comprise at least one physical solvent selected from among the group made up of methanol, ethanol, 2-ethoxyethanol, triethylene glycoldimethylether, tetraethylene glycoldimethylether, pentaethylene glycoldimethylether, hexaethylene glycoldimethylether, heptaethylene glycol-dimethylether, octaethylene glycoldimethylether, diethylene glycol butoxyacetate, glycerol triacetate, sulfolane, N-methylpyrrolidone, N-methylmorpholin-3-one, N,N-dimethylformamide, N-formylmorpholine, N,N-dimethyl-imidazolidin-2-one, N-methylimidazole, ethylene glycol, diethylene glycol, triethylene glycol, thiodiglycol and tributyl phosphate.

The gaseous effluent can be selected from among natural gas, syngases, combustion fumes, refinery gas, acid gas from an amine plant, Claus tail gas, biomass fermentation gas, cement plant gas and incinerator fumes.

The method according to the invention can be implemented for selectively removing the $H_2S$ over the $CO_2$ from a gaseous effluent comprising $H_2S$ and $CO_2$, preferably natural gas.

BRIEF DESCRIPTION OF THE SOLE FIGURE

Other features and advantages of the invention will be clear from reading the description hereafter of embodiments given by way of non limitative example, with reference to the accompanying FIGURE described hereafter:

FIG. 1 is a block diagram of the implementation of an acid gas treating method.

In the diagrams of the present description illustrating the preparation of nitrogen compounds according to the invention, the arrows represent reaction stages. These are reaction schemes.

DETAILED DESCRIPTION OF THE INVENTION

The novel nitrogen compounds according to the invention are tertiary diamines meeting general formula (I) as follows:

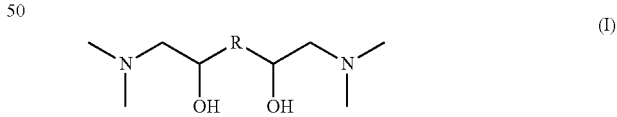

wherein R is an alkanediyl radical —$(CH_2)n$- with n=2, 3, 4, 5 or 6.

In the present description, a tertiary diamine is understood to be a chemical compound comprising two amine functions which are tertiary amine functions.

In general formula (I), the hydroxyl groups are carried by carbon atoms at amine beta position.

R is selected from among one of the following groups:
r1: a 1,2-ethanediyl radical —$CH_2$—$CH_2$— when n=2. The nitrogen compound is then N,N,N',N'-(tetramethyl)-1,6-diamino-2,5-hexanediol having the following formula:

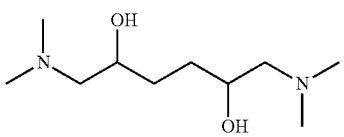

r2: a 1,4-butanediyl radical —CH$_2$—CH$_2$—CH$_2$—CH$_2$— when n=4. The nitrogen compound is then N,N,N',N'-(tetramethyl)-1,8-diamino-2,7-octanediol having the following formula:

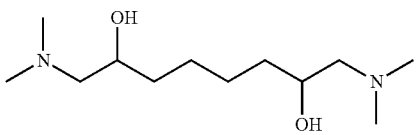

r3: a 1,3-propanediyl radical when n=3. The nitrogen compound is then N,N,N',N'-tetramethyl-1,7-diamino-2,6-heptanediol having the following formula:

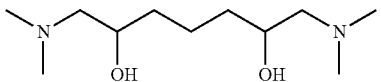

r4: a 1,5-pentanediyl radical when n=5. The nitrogen compound is then N,N,N',N'-tetramethyl-1,9-diamino-2,8-nonanediol having the following formula:

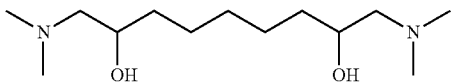

r5: a 1,6-hexanediyl radical when n=6. The nitrogen compound is then N,N,N',N'-tetramethyl-1,10-diamino-2,9-decanediol having the following formula:

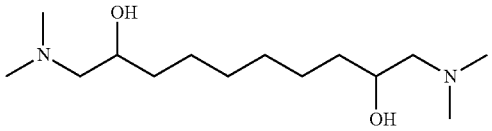

Advantageously, a compound according to the invention is N,N,N',N'-(tetra-methyl)-1,6-diamino-2,5-hexanediol or N,N,N',N'-(tetramethyl)-1,8-diamino-2,7-octanediol.

Synthesis of a Compound According to the Invention

The nitrogen compounds of general formula (I) can be prepared by carrying out the following reactions:
- a first epoxidation reaction of an alpha-omega-diene to achieve epoxidation of each one of the alkene functions of the alpha-omega-diene to oxirane functions so as to produce a diepoxyalkane,
- a second reaction of addition of two moles of dimethylamine and one molecule of the diepoxyalkane so as to produce the nitrogen compound according to general formula (I).

An alpha-omega-diene is understood to be a diene comprising two alkene functions at the ends, such as 1,5-hexadiene and 1,7-octadiene.

The synthesis of N,N,N',N'-(tetramethyl)-1,6-diamino-2,5-hexanediol is illustrated by Diagram A hereafter:

Diagram A: Preparation of the N,N,N',N'-(tetramethyl)-1,6-diamino-2,5-hexanediol compound

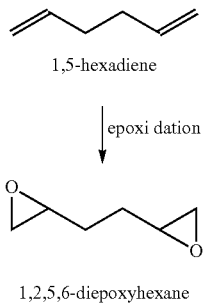

N,N,N',N'-tetramethyl-1,6-diamino-2,5-hexanediol

A reaction of epoxidation of each one of the two alkene functions of the 1,5-hexadiene to oxirane functions is first conducted in order to obtain 1,2,5,6-diepoxyhexane. This epoxidation reaction can be carried out with any means known to the person skilled in the art for conducting epoxidation of a carbon-carbon double bond. A peroxide, a hydroperoxide, a peracid such as peracetic acid or 3-chloroperbenzoic acid, or a perester can be used for example. It is also possible to use the combination of an acid such as acetic acid and of a peroxide such as hydrogen peroxide allowing in-situ generation of a peracid. The reaction can be conducted under mild conditions, for example at a temperature close to ambient temperature, and in the presence of a solvent, which can be a chlorinated solvent such as dichloromethane or an aliphatic or aromatic hydrocarbon solvent. The epoxidation reaction of an unsaturation can also be performed by means of oxygen and of a suitable catalytic system.

Secondly, a reaction of addition of two moles of dimethylamine to one molecule of 1,2,5,6-diepoxyhexane to form N,N,N',N'-(tetramethyl)-1,6-diamino-2,5-hexanediol is carried out. This reaction can be conducted with excess dimethylamine. It is an exothermic reaction that is preferably performed with suitable temperature control. For example, the temperature is maintained within the −15° C./100° C. range.

The synthesis of N,N,N',N'-(tetramethyl)-1,8-diamino-2,7-octanediol is illustrated by Diagram B below:

Diagram B: Preparation of the N,N,N',N'-(tetramethyl)-1,8-diamino-2,7-octanediol compound

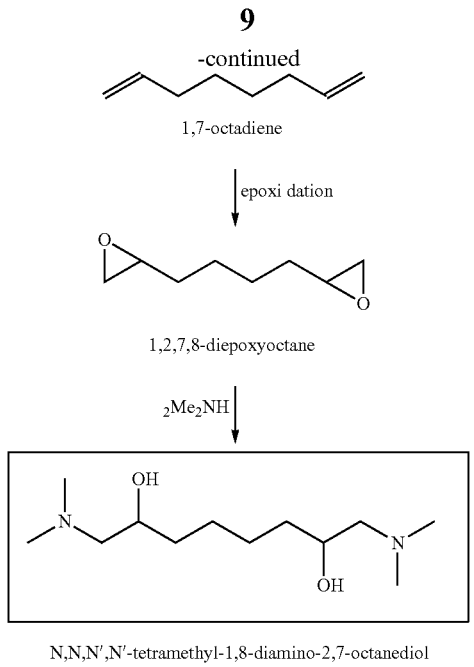

1,7-octadiene

↓ epoxidation 1,2,7,8-diepoxyoctane

↓ 2Me₂NH

N,N,N',N'-tetramethyl-1,8-diamino-2,7-octanediol

This synthesis is based on the same reactions, the same procedures and the same conditions as those described above for preparing N,N,N',N'-(tetramethyl)-1,6-diamino-2,5-hexanediol, but using 1,7-octadiene instead of 1,5-hexadiene as the precursor for the first epoxidation reaction. The epoxidation reaction yields 1,2,7,8-diepoxyoctane used in the second addition reaction with dimethylamine.

The synthesis of the other compounds according to the invention, N,N,N',N'-tetramethyl-1,7-diamino-2,6-heptanediol (R=r3, n=3), N,N,N',N'-tetramethyl-1,9-diamino-2,8-nonanediol (R=r4, n=5) and N,N,N',N'-tetramethyl-1,10-diamino-2,9-decanediol (R=r5, n=6), is based on the same reactions, the same procedures and the same conditions as those described above for preparing N,N,N',N'-(tetramethyl)-1,6-diamino-2,5-hexanediol or N,N,N',N'-(tetramethyl)-1,8-diamino-2,7-octanediol, but by using the compounds listed in Table 1 below as the precursors and intermediate products of the reactions:

TABLE 1

| Name of the compound of general formula(I) | Name of the alpha-omega-diene | Name of the diepoxyalkane |
| --- | --- | --- |
| N,N,N',N'-tetramethyl-1,7-diamino-2,6-heptanediol | 1,6-heptadiene | 1,2,6,7-diepoxyheptane |
| N,N,N',N'-tetramethyl-1,9-diamino-2,8-nonanediol | 1,8-nonadiene | 1,2,8,9-diepoxynonane |
| N,N,N',N'-tetramethyl-1,10-diamino-2,9-decanediol | 1,9-decadiene | 1,2-9,10-diepoxydecane |

Preferably, the first epoxidation reaction and the second addition reaction are conducted in two successive stages during the preparation of the nitrogen compounds according to the invention.

Use of the Compounds According to the Invention in the Treatment of Gaseous Effluents The compounds according to the invention can be used in different fields of chemistry and they can be advantageously used in the treatment of gas of industrial origin and of natural gas.

The present invention aims to remove acid compounds from a gaseous effluent using an aqueous solution comprising at least one nitrogen compound according to general formula (I), and advantageously N,N,N',N'-(tetramethyl)-1,6-diamino-2,5-hexanediol and N,N,N',N'-(tetramethyl)-1,8-diamino-2,7-octanediol. The solution is contacted with the gaseous effluent to remove acid compounds contained therein.

The method of removing acid compounds contained in a gaseous effluent according to the invention can in particular be implemented for selective removal of $H_2S$ over $CO_2$ from a gaseous effluent comprising $H_2S$ and $CO_2$, for example natural gas.

The method of removing acid compounds contained in a gaseous effluent according to the invention can also be advantageously implemented for $CO_2$ capture from gas of industrial origin and from natural gas, for example combustion fumes.

Using beta-hydroxylated tertiary diamines according to the invention allows to obtain good performances in terms of cyclic capacity of acid gas absorption and/or of absorption selectivity towards $H_2S$, notably higher absorption selectivity towards $H_2S$ than reference amines such as N-methyldiethanolamine (MDEA) for an equivalent or higher acid gas cyclic absorption capacity.

Composition of the Absorbent Solution

The absorbent solution used for removing the acid compounds contained in a gaseous effluent comprises:
water,
at least one nitrogen compound belonging to the family of tertiary diamines meeting general formula (I).

The absorbent solution can comprise N,N,N',N'-(tetramethyl)-1,6-diamino-2,5-hexanediol or N,N,N',N1'-(tetramethyl)-1,8-diamino-2,7-octanediol, or a mixture of the two compounds.

The amines of general formula (I) can be in variable concentration in the absorbent solution, ranging for example between 5 wt. % and 95 wt. %, preferably between 10 wt. % and 90 wt. %, more preferably between 20 wt. % and 60 wt. %, and most preferably between 25 wt. % and 50 wt. %, inclusive.

The absorbent solution can contain between 5 wt. % and 95 wt. % of water, preferably between 10 wt. % and 90 wt. %, more preferably between 40 wt. % and 80 wt. %, and most preferably between 50 wt. % and 75 wt. %, inclusive.

The sum of the mass fractions expressed in wt. % of the various compounds of the absorbent solution is 100 wt. % of the absorbent solution.

According to one embodiment, the absorbent solution can furthermore contain at least one additional amine that is a tertiary amine, such as N-methyldiethanolamine, triethanolamine, diethylmonoethanolamine, dimethylmonoethanolamine or ethyldiethanolamine, or a secondary amine with severe steric hindrance, this hindrance being defined by either the presence of two secondary carbons at nitrogen alpha position or at least one tertiary carbon at nitrogen alpha position. Said additional amine is understood to be any compound having at least one severely hindered tertiary or secondary amine function. The concentration of said severely hindered tertiary or secondary additional amine in the absorbent solution can range between 5 wt. % and 95 wt. %, preferably between 5 wt. % and 50 wt. %, more preferably between 5 wt. % and 30 wt. %.

According to an embodiment, the amines of general formula (I) can be formulated with one or more compounds containing at least one primary or secondary amine function. For example, the absorbent solution comprises up to a concentration of 30 wt. %, preferably below 15 wt. % and more preferably below 10 wt. % of said compound containing at least one primary or secondary amine function. Preferably, the absorbent solution comprises at least 0.5 wt. % of said compound containing at least one primary or secondary amine function. Said compound allows to accelerate the absorption kinetics of the $CO_2$ and, in some cases, of the COS contained in the gas to be treated.

A non-exhaustive list of compounds containing at least one primary or secondary amine function that can go into the formulation is given below:
- monoethanolamine,
- diethanolamine,
- N-butylethanolamine,
- aminoethylethanolamine,
- diglycolamine,
- piperazine,
- 1-methylpiperazine,
- 2-methylpiperazine,
- homopiperazine,
- N-(2-hydroxyethyl)piperazine,
- N-(2-aminoethyl)piperazine,
- morpholine,
- 3-(metylamino)propylamine,
- 1,6-hexanediamine and all the diversely N-alkylated derivatives thereof such as, for example, N,N-dimethyl-1,6-hexanediamine, N,N'-dimethyl-1,6-hexanediamine, N-methyl-1,6-hexanediamine or N,N',N'-trimethyl-1,6-hexanediamine.

The absorbent solution comprising at least one compound according to the invention can contain a mixture of additional amines as defined above.

According to an embodiment, the absorbent solution can contain organic compounds non reactive towards the acid compounds (commonly referred to as "physical solvents"), which allow to increase the solubility of at least one or more acid compounds of the gaseous effluent. For example, the absorbent solution can comprise between 5 wt. % and 50 wt. % of physical solvent such as alcohols, ethers, ether alcohols, glycol and polyethylene glycol ethers, glycol thioethers, glycol and polyethylene glycol esters and alkoxyesters, glycerol esters, lactones, lactames, N-alkylated pyrrolidones, morpholine derivatives, morpholin-3-one, imidazoles and imidazolidinones, N-alkylated piperidones, cyclotetramethylenesulfones, N-alkylformamides, N-alkylacetamides, ether-ketones, alkyl carbonates or alkyl phosphates and derivatives thereof.

By way of non limitative example, it can be methanol, ethanol, 2-ethoxyethanol, triethylene glycoldimethylether, tetraethylene glycoldimethylether, pentaethylene glycol-dimethylether, hexaethylene glycoldimethylether, heptaethylene glycol-dimethylether, octaethylene glycoldimethylether, diethylene glycol butoxyacetate, glycerol triacetate, sulfolane, N-methylpyrrolidone, N-methylmorpholin-3-one, N,N-dimethylformamide, N-formyl-morpholine, N,N-dimethyl-imidazolidin-2-one, N-methylimidazole, ethylene glycol, diethylene glycol, triethylene glycol, thiodiglycol, propylene carbonate, tributylphosphate.

Nature of the Gaseous Effluents

The absorbent solutions comprising at least one nitrogen compound according to the invention can be used for deacidizing the following gaseous effluents: natural gas, syngas, combustion fumes, refinery gas, acid gas from an amine plant, Claus tail gas, biomass fermentation gas, cement plant gas and incinerator fumes. These gaseous effluents contain one or more of the following acid compounds: $CO_2$, $H_2S$, mercaptans (for example methylmercaptan ($CH_3SH$), ethylmercaptan ($CH_3CH_2SH$), propylmercaptan ($CH_3CH_2CH_2SH$)), COS, $CS_2$, $SO_2$.

Combustion fumes are produced notably by the combustion of hydrocarbons, biogas, coal in a boiler or for a combustion gas turbine, for example in order to produce electricity. By way of illustration, a deacidizing method using the compounds according to the invention can be implemented for absorbing at least 70%, preferably at least 80% or even at least 90% of the $CO_2$ contained in combustion fumes. These fumes generally have a temperature ranging between 20° C. and 60° C., a pressure ranging between 1 and 5 bar, and they can comprise between 50 and 80% nitrogen, between 5 and 40% carbon dioxide, between 1 and 20% oxygen, and some impurities such as SOx and NOx if they have not been removed upstream from the deacidizing process. In particular, the deacidizing method using the compounds according to the invention is particularly well suited for absorbing the $CO_2$ contained in combustion fumes having a low $CO_2$ partial pressure, for example a $CO_2$ partial pressure below 200 mbar.

The deacidizing method using the compounds according to the invention can be implemented for deacidizing a syngas. Syngas contains carbon monoxide CO, hydrogen $H_2$ (generally with a $H_2$/CO ratio of 2), water vapour (generally at saturation at the wash temperature) and carbon dioxide $CO_2$ (of the order of 10%). The pressure generally ranges between 20 and 30 bar, but it can reach up to 70 bar. It can also comprise sulfur-containing ($H_2S$, COS, etc.), nitrogen-containing ($NH_3$, HCN) and halogenated impurities.

The deacidizing method using the compounds according to the invention can be implemented for deacidizing a natural gas. Natural gas predominantly consists of gaseous hydrocarbons, but it can contain some of the following acid compounds: $CO_2$, $H_2S$, mercaptans, COS, $CS_2$. The proportion of these acid compounds is very variable and it can reach up to 70 vol. % for $CO_2$ and up to 40 vol. % for $H_2S$. The temperature of the natural gas can range between 20° C. and 100° C. The pressure of the natural gas to be treated can range between 10 and 200 bar. The invention can be implemented in order to reach specifications generally imposed on deacidized gas, which are less than 2% $CO_2$, or even less than 50 ppm $CO_2$ so as to subsequently carry out liquefaction of the natural gas, less than 4 ppm $H_2S$, and less than 50 ppm or even less than 10 ppm by volume of total sulfur.

Method of Removing Acid Compounds from a Gaseous Effluent

Using an aqueous solution comprising a compound according to general formula (I) for deacidizing a gaseous effluent is schematically done by carrying out an absorption stage followed by a regeneration stage, as shown in FIG. 1 for example.

With reference to FIG. 1, the plant for deacidizing a gaseous effluent according to the invention comprises an absorption column C1 provided with means for contacting the gas and the liquid, for example a random packing, a structured packing or trays. The gaseous effluent to be treated is fed through a line 1 opening into the bottom of column C1. A line 4 allows the absorbent solution to be fed to the top of column C1. A line 2 allows the treated (deacidized) gas to be discharged and a line 3 allows the absorbent solution enriched in acid compounds following absorption to be sent to a regeneration column C2. This regeneration column C2 is provided with gas-liquid contacting internals, for example trays, random or structured packings. The bottom of column C2 is equipped with a reboiler R1 that provides the heat required for regeneration by vaporizing a fraction of the absorbent solution. The acid compound-enriched solution is fed to the top of regeneration column C2 through a line 5. A line 7 allows to discharge at the top of column C2 the gas enriched in acid compounds released upon regeneration, and a line 6 arranged in the bottom of column C2 allows the regenerated absorbent solution to be sent to absorption column C1. A heat exchanger E1 allows the heat of the regenerated absorbent solution from column C2 to be recovered so as to heat the acid compound-enriched absorbent solution leaving absorption column C1.

The absorption stage consists in contacting the gaseous effluent delivered through line 1 with the absorbent solution delivered through line 4. Upon contact, the amine functions of the molecules according to general formula (I) of the absorbent solution react with the acid compounds contained in the effluent so as to obtain an acid compound-depleted gaseous effluent that is discharged through line 2 at the top of column C1 and an acid compound-enriched absorbent solution that is discharged through line 3 in the bottom of column C1 to be regenerated.

The acid compound absorption stage can be carried out at a pressure in column C1 ranging between 1 and 200 bar, preferably between 1 and 120 bar, more preferably between 20 and 100 bar for natural gas treatment, preferably between 1 and 3 bar for industrial fumes treatment, and at a temperature in column C1 ranging between 20° C. and 100° C., preferably between 30° C. and 90° C., or even between 30° C. and 60° C.

The regeneration stage notably consists in heating and optionally in expanding the acid compound-enriched absorbent solution so as to release the acid compounds in gas form. The acid compound-enriched absorbent solution leaving column C1 is fed to heat exchanger E1 where it is heated by the stream circulating in line 6 and coming from regeneration column C2. The heated solution at the outlet of E1 is fed to regeneration column C2 through line 5.

In regeneration column C2, under the effect of contacting the absorbent solution flowing in through line 5 with the vapour produced by the reboiler, the acid compounds are released in gas form and discharged at the top of column C2 through line 7. The regenerated absorbent solution, i.e. depleted in acid compounds, is discharged through line 6 and cooled in E1, then recycled to absorption column C1 through line 4.

The regeneration stage can be carried out by thermal regeneration, optionally complemented by one or more expansion stages. For example, the acid compound-enriched absorbent solution discharged through line 3 can be sent to a first flash drum (not shown) prior to being sent to heat exchanger E1. In the case of natural gas, expansion allows to obtain a gas discharged at the top of the drum that contains the major part of the aliphatic hydrocarbons co-absorbed by the absorbent solution. This gas can be optionally washed by a fraction of the regenerated absorbent solution and the gas thus obtained can be used as fuel gas. The flash drum preferably operates at a pressure lower than in absorption column C1 and higher than in regeneration column C2. This pressure is generally determined by the conditions of use of the fuel gas, and it is typically of the order of 5 to 15 bar. The flash drum operates at a temperature substantially identical to the temperature of the absorbent solution obtained in the bottom of absorption column C1.

Regeneration can be carried out at a pressure in column C2 ranging between 1 and 5 bar, or even up to 10 bar, and at a temperature in column C2 ranging between 100° C. and 180° C., preferably between 110° C. and 170° C., more preferably between 120° C. and 140° C. Preferably, the regeneration temperature in column C2 ranges between 155° C. and 180° C. in cases where the acid gases are intended to be reinjected. Preferably, the regeneration temperature in column C2 ranges between 115° C. and 130° C. in cases where the acid gas is sent to the atmosphere or to a downstream treating process such as a Claus process or a tail gas treating process.

EXAMPLES

The examples below illustrate by way of non limitative example the synthesis of the compounds according to the invention, and some performances of these compounds when used in aqueous solution for removing acid compounds such as $CO_2$ or $H_2S$ contained in a gaseous effluent by contacting the gaseous effluent with the solution.

Example 1: Synthesis of the Molecules According to the Invention

The examples hereafter illustrate the synthesis of the nitrogen compounds according to the invention, it being understood that all the synthesis possibilities for these molecules, regarding synthesis routes as well as the possible operating modes, are not described here.

Example of N,N,N',N'-(tetramethyl)-1,6-diamino-2,5-hexanediol Synthesis 460.9 g (2.67 mol) of 3-chloroperbenzoic acid is added in four hours, in small fractions, to a solution of 75.0 g of 1,5-hexadiene in 1200 ml dichloromethane maintained between 0° C. and 5° C. After return to ambient temperature, the medium is filtered. The filtrate is washed twice with 750 ml of an aqueous 10% sodium sulfite solution, then with 750 ml of water. After distillation, 86.1 g of a product whose $^{13}C$ NMR spectrum ($CDCl_3$) characterized by the below data matches that of 1,2,5,6-diepoxyhexane is obtained:
46.1 ppm: [$CH_2(O)CH$]—$CH_2$—$CH_2$—[$CH(O)CH_2$]
50.8 ppm: [$CH_2(O)CH$]—$CH_2$—$CH_2$—[$CH(O)CH_2$]
28.6 ppm: [$CH_2(O)CH$]—$CH_2$—$CH_2$—[$CH(O)CH_2$]
28.2 ppm: [$CH_2(O)CH$]—$CH_2$—$CH_2$—[$CH(O)CH_2$]
51.0 ppm: [$CH_2(O)CH$]—$CH_2$—$CH_2$—[$CH(O)CH_2$]
46.1 ppm: [$CH_2(O)CH$]—$CH_2$—$CH_2$—[$CH(O)CH_2$].

85.0 g (0.74 mol) of 1,2,5,6-diepoxyhexane is added in two hours, while maintaining the temperature at 5° C., to 1636.0 g of an aqueous 40% dimethylamine solution. After return to ambient temperature, the excess dimethylamine and the water are removed. After distillation under reduced pressure, 115.0 g of a product whose $^{13}C$ NMR spectrum ($CDCl_3$) characterized by the below data matches that of N,N,N',N'-(tetramethyl)-1,6-diamino-2,5-hexanediol is isolated.
45.3 ppm: $(CH_3)_2N$—$CH_2$—$CH(OH)$—$CH_2$—$CH_2$—$CH(OH)$—$CH_2$—$N(CH_3)_2$
30.8 ppm: $(CH_3)_2N$—$CH_2$—$CH(OH)$—$CH_2$—$CH_2$—$CH(OH)$—$CH_2$—$N(CH_3)_2$
67.0 ppm: $(CH_3)_2N$—$CH_2$—$CH(OH)$—$CH_2$—$CH_2$—$CH(OH)$—$CH_2$—$N(CH_3)_2$
65.3 ppm: $(CH_3)_2N$—$CH_2$—$CH(OH)$—$CH_2$—$CH_2$—$CH(OH)$—$CH_2$—$N(CH_3)_2$
65.3 ppm: $(CH_3)_2N$—$CH_2$—$CH(OH)$—$CH_2$—$CH_2$—$CH(OH)$—$CH_2$—$N(CH_3)_2$
66.7 ppm: $(CH_3)_2N$—$CH_2$—$CH(OH)$—$CH_2$—$CH_2$—$CH(OH)$—$CH_2$—$N(CH_3)_2$
31.1 ppm: $(CH_3)_2N$—$CH_2$—$CH(OH)$—$CH_2$—$CH_2$—$CH(OH)$—$CH_2$—$N(CH_3)_2$ 45.3 ppm: $(CH_3)_2N-CH_2-CH(OH)-CH_2-CH_2-CH(OH)-CH_2-N(CH_3)_2$ Example of N,N,N',N'-(tetramethyl)-1,8-diamino-2,7-octanediol Synthesis 457.5 g (2.65 mol) of 3-chloroperbenzoic acid is added in four hours, in small fractions, to a solution of 100.0 g of 1,7-octadiene in 1200 ml dichloromethane maintained between 0° C. and 5° C. After return to ambient temperature, the medium is filtered. The filtrate is washed twice with 750 ml of an aqueous 10% sodium sulfite solution, then with 750 ml of water. After distillation, 110.0 g of a product whose $^{13}C$ NMR spectrum ($CDCl_3$) characterized by the below data matches that of 1,2,7,8-diepoxyoctane is obtained:

45.6 ppm:[CH2(O)CH]—CH2-CH2-CH2-CH2-[CH(O)CH2]

50.8 ppm:[CH2(O)CH]—CH2-CH2-CH2-CH2-[CH(O)CH2]

31.4 ppm:[CH2(O)CH]—CH2-CH2-CH2-CH2-[CH(O)CH2]

24.9 ppm:[CH2(O)CH]—CH2-CH2-CH2-CH2-[CH(O)CH2]

24.9 ppm:[CH2(O)CH]—CH2-CH2-CH2-CH2-[CH(O)CH2]

31.4 ppm:[CH2(O)CH]—CH2-CH2-CH2-CH2-[CH(O)CH2]

50.8 ppm:[CH2(O)CH]—CH2-CH2-CH2-CH2-[CH(O)CH2]

45.6 ppm:[CH2(O)CH]—CH2-CH2-CH2-CH2-[CH(O)CH2].

100.0 g (0.70 mol) of 1,2,7,8-diepoxyoctane is added in two hours, while maintaining the temperature at 5° C., to 769.0 g of an aqueous 40% dimethylamine solution. After return to ambient temperature, the excess dimethylamine and the water are removed. After distillation under reduced pressure, 143.0 g of a product whose $^{13}C$ NMR spectrum ($CDCl_3$) characterized by the below data matches that of N,N,N',N'-(tetramethyl)-1,8-diamino-2,7-octanediol is isolated.

45.3 ppm: (CH3)2N—CH2-CH(OH)—CH2-CH2-CH2-CH2-CH(OH)—CH2-N(CH3)2

65.4 ppm: (CH3)2N—CH2-CH(OH)—CH2-CH2-CH2-CH2-CH(OH)—CH2-N(CH3)2

66.7 ppm: (CH3)2N—CH2-CH(OH)—CH2-CH2-CH2-CH2-CH(OH)—CH2-N(CH3)2

34.7 ppm: (CH3)2N—CH2-CH(OH)—CH2-CH2-CH2-CH2-CH(OH)—CH2-N(CH3)2

25.7 ppm: (CH3)2N—CH2-CH(OH)—CH2-CH2-CH2-CH2-CH(OH)—CH2-N(CH3)2

25.7 ppm: (CH3)2N—CH2-CH(OH)—CH2-CH2-CH2-CH2-CH(OH)—CH2-N(CH3)2

34.7 ppm: (CH3)2N—CH2-CH(OH)—CH2-CH2-CH2-CH2-CH(OH)—CH2-N(CH3)2

66.7 ppm: (CH3)2N—CH2-CH(OH)—CH2-CH2-CH2-CH2-CH(OH)—CH2-N(CH3)2

65.4 ppm: (CH3)2N—CH2-CH(OH)—CH2-CH2-CH2-CH2-CH(OH)—CH2-N(CH3)2

45.3 ppm: (CH3)2N—CH2-CH(OH)—CH2-CH2-CH2-CH2-CH(OH)—CH2-N(CH3)2.

Example 2: $CO_2$ Absorption Rate of an Amine Formulation for a Selective Absorption Method Comparative $CO_2$ absorption tests are carried out with different absorbent solutions:
- an absorbent solution comprising 49 wt. % N,N,N',N'-(tetramethyl)-1,6-diamino-2,5-hexanediol according to the invention in water,
- an aqueous solution of N-methyldiethanolamine (MDEA) with 47 wt. % MDEA, which is the reference absorbent solution for selective removal in gas treatment,
- an aqueous solution of 1,2-bis-(pyrrolidinylethoxy)-ethane with 50 wt. % 1,2-bis-(pyrrolidinylethoxy)-ethane, which is a diaminoether with two tertiary amine functions according to the general formula of U.S. Pat. No. 4,405,582 but has no alcohol function and does not fall within general formula (I) according to the invention,
- an aqueous solution of 1,2-bis-(tertiobutylaminoethoxy)-ethane with 40 wt. % 1,2-bis-(tertiobutylaminoethoxy)-ethane, which is a diaminoether with two secondary functions having severe steric hindrance of the nitrogen atoms according to the general formula of U.S. Pat. No. 4,405,583, with no alcohol function and which does not fall within general formula (I) according to the invention,
- an aqueous solution of N,N,N',N'-tetramethyl-1,6-hexanediamine (TMHDA) with 50 wt. % TMHDA, which is a tertiary diamine disclosed in patent FR-2,934,172, but which has no alcohol function and does not fall within general formula (I) according to the invention.

For each test, the $CO_2$ flow absorbed by the aqueous absorbent solution is measured in a closed reactor of Lewis cell type. 200 g solution is fed into the closed reactor at a controlled temperature of 50° C. Four successive $CO_2$ injections are carried out from 100 to 200 mbar in the vapour phase of the 200 $cm^3$-volume reactor. The gas phase and the liquid phase are stirred at 100 rpm and entirely characterized from the hydrodynamic point of view. For each injection, the $CO_2$ absorption rate is measured through pressure variation in the gas phase. A global transfer coefficient Kg is thus determined using a mean of the results obtained for the four injections.

The results obtained are shown in Table 2 hereafter in relative absorption rate by comparison with the reference aqueous absorbent solution comprising 47 wt. % MDEA, this relative absorption rate being defined by the ratio of the global transfer coefficient of the absorbent solution tested to the global transfer coefficient of the reference absorbent solution (with MDEA).

TABLE 2

| Compound | Concentration (wt. %) | $CO_2$ relative absorption rate at 50° C. |
|---|---|---|
| MDEA | 47 | 1.00 |
| 1,2-bis-(pyrrolidinylethoxy)-ethane (according to U.S. Pat. No. 4,405,582) | 50 | 1.43 |
| 1,2-bis-(tertiobutylaminoethoxy)-ethane (according to U.S. Pat. No. 4,405,583) | 40 | 1.74 |
| TMHDA (according to FR-2,934,172) | 50 | 2.72 |
| N,N,N',N'-(tetramethyl)-1,6-diamino-2,5-hexanediol | 49 | 0.87 |

The results show, under these test conditions, a slower rate of absorption of $CO_2$ by the absorbent solution according to the invention compared to the reference formulation with MDEA and compared to the absorbent solutions with some molecules of the prior art. It therefore appears that the exemplified compound according to the invention surprisingly is of particular and improved interest in the case of selective deacidizing of a gaseous effluent where the $CO_2$ absorption kinetics is to be limited.

Example 3: $H_2S$ Absorption Capacity of a N,N,N', N'-(tetramethyl)-1,6-diamino-2,5-hexanediol Formulation for an Acid Gas Treating Method The $H_2S$ absorption capacity performances at 40° C. of an aqueous solution of N,N,N',N'-(tetramethyl)-1,6-diamino-2, 5-hexanediol according to the invention, containing 49 wt. % N,N,N',N'-(tetramethyl)-1,6-diamino-2,5-hexanediol, are compared with those of an MDEA aqueous solution containing 50 wt. % MDEA, which is a reference absorbent solution for deacidizing $H_2S$-containing gas.

An absorption test is carried out at 40° C. on aqueous amine solutions in a thermostat-controlled equilibrium cell. This test consists in injecting into the equilibrium cell, previously filled with degassed aqueous amine solution, a known amount of acid gas, $H_2S$ in this example, then in waiting for the equilibrium state to be reached. The amounts of acid gas absorbed in the aqueous amine solution are then deduced from the temperature and pressure measurements by means of material and volume balances. The solubilities are conventionally represented in form of $H_2S$ partial pressures (in bar) as a function of the $H_2S$ loading (in mol of $H_2S$/kg absorbent solution and in mol of $H_2S$/mol of amine).

In the case of deacidizing in natural gas treatment, the $H_2S$ partial pressures encountered in acid gases typically range between 0.1 and 1 bar at a temperature of 40° C. By way of example, in this industrial range, Table 3 hereafter compares the $H_2S$ loadings obtained at 40° C. for various $H_2S$ partial pressures between the 50 wt. % MDEA absorbent solution and the 49 wt. % N,N,N',N'-(tetramethyl)-1, 6-diamino-2,5-hexanediol absorbent solution.

TABLE 3

| $H_2S$ partial pressure (bar) | 49 wt. % N,N,N',N'-(tetramethyl)-1,6-diamino-2,5-hexanediol aqueous solution at 40° C. | | 50 wt. % MDEA aqueous solution at 40° C. | |
|---|---|---|---|---|
| | $H_2S$ loading (mol/mol amine) | $H_2S$ loading (mol/kg) | $H_2S$ loading (mol/mol amine) | $H_2S$ loading (mol/kg) |
| 0.10 | 0.94 | 2.26 | 0.21 | 0.88 |
| 1.00 | 1.75 | 4.20 | 0.69 | 2.95 |

At 40° C., whatever the $H_2S$ partial pressure, the absorption capacity of the N,N,N',N'-(tetramethyl)-1,6-diamino-2, 5-hexanediol aqueous solution according to the invention is higher than that of the MDEA solution. At a $H_2S$ partial pressure of 0.10 bar, the difference between the $H_2S$ loadings of the two absorbent solutions is 1.38 mol/kg, with an absorption capacity for the N,N,N',N'-(tetramethyl)-1,6-diamino-2,5-hexanediol absorbent solution increased by 157% in relation to the reference MDEA absorbent solution. At a $H_2S$ partial pressure of 1 bar, the $H_2S$ loading increase for the N,N,N',N'-(tetramethyl)-1,6-diamino-2,5-hexanediol absorbent solution still is 42% in relation to the reference MDEA absorbent solution. It can thus be observed that the 49 wt. % N,N,N',N'-(tetramethyl)-1,6-diamino-2,5-hexanediol aqueous solution has a higher $H_2S$ absorption capacity than the reference 50 wt. % MDEA aqueous solution at 40° C., in the $H_2S$ partial pressure range between 0.1 and 1 bar corresponding to a partial pressure range representative of usual industrial conditions.

It thus appears that this exemplified molecule according to the invention allows to reduce the absorbent solution flow rates required in $H_2S$-containing gas deacidizing applications compared to the reference MDEA absorbent solution.

$CO_2$ absorption being slower in an aqueous solution of N,N,N',N'-(tetramethyl)-1,6-diamino-2,5-hexanediol than in a MDEA aqueous solution (see Example 2 above) and the acid gas, notably $H_2S$, absorption capacity being equivalent or higher with the N,N,N',N'-(tetramethyl)-1,6-diamino-2,5-hexanediol absorbent solution in relation to a MDEA aqueous solution as illustrated in the present example, it appears that this exemplified molecule according to the invention allows to reduce the absorbent solution flow rates required in selective deacidizing applications ($H_2S/CO_2$) for absorbing a given flow of $H_2S$ while reducing the flow of co-absorbed $CO_2$ in relation to the reference MDEA absorbent solution.

Example 4: $H_2S$ Absorption Capacity of a N,N,N', N'-(tetramethyl)-1,8-diamino-2,7-octanediol Formulation for an Acid Gas Treating Method The $H_2S$ absorption capacity performances at 40° C. of an aqueous solution of N,N,N',N'-(tetramethyl)-1,8-diamino-2, 7-octanediol according to the invention containing 50 wt. % of N,N,N',N'-(tetramethyl)-1,8-diamino-2,7-octanediol are compared with those of an MDEA aqueous solution containing 50 wt. % MDEA, which is a reference absorbent solution for deacidizing $H_2S$-containing gas.

An absorption test is carried out at 40° C. according to the operating mode described in the previous example.

In the case of natural gas treatment deacidizing, the $H_2S$ partial pressures encountered in acid gases typically range between 0.1 and 1 bar, at a temperature of 40° C. By way of example, in this industrial range, Table 4 hereafter compares the $H_2S$ loadings obtained at 40° C. for various $H_2S$ partial pressures between the 50 wt. % MDEA absorbent solution and the 50 wt. % N,N,N',N'-(tetramethyl)-1,8-diamino-2,7-octanediol absorbent solution.

TABLE 4

| $H_2S$ partial pressure (bar) | 50 wt. % N,N,N',N'-(tetramethyl)-1,8-diamino-2,7-octanediol aqueous solution at 40° C. | | 50 wt. % MDEA aqueous solution at 40° C. | |
|---|---|---|---|---|
| | $H_2S$ loading (mol/mol amine) | $H_2S$ loading (mol/kg) | $H_2S$ loading (mol/mol amine) | $H_2S$ loading (mol/kg) |
| 0.10 | 1.04 | 2.25 | 0.21 | 0.88 |
| 1.00 | 1.82 | 3.92 | 0.69 | 2.95 |

At 40° C., whatever the $H_2S$ partial pressure, the absorption capacity of the N,N,N',N'-(tetramethyl)-1,8-diamino-2, 7-octanediol aqueous solution according to the invention is higher than that of the MDEA solution. At a $H_2S$ partial pressure of 0.10 bar, the difference between the $H_2S$ loadings of the two absorbent solutions is 1.37 mol/kg, with an absorption capacity for the N,N,N',N'-(tetramethyl)-1,8-diamino-2,7-octanediol absorbent solution increased by 156% in relation to the reference MDEA absorbent solution. At a $H_2S$ partial pressure of 1 bar, the $H_2S$ loading increase for the N,N,N',N'-(tetramethyl)-1,8-diamino-2,7-octanediol absorbent solution still is 33% in relation to the reference MDEA absorbent solution. It can thus be observed that the 50 wt. % N,N,N',N'-(tetramethyl)-1,8-diamino-2,7-octanediol aqueous solution has a higher $H_2S$ absorption capacity than the reference 50 wt. % MDEA aqueous solution at 40° C., in the $H_2S$ partial pressure range between 0.1 and 1 bar corresponding to a partial pressure range representative of usual industrial conditions.

It therefore appears that the exemplified molecule according to the invention allows to reduce the absorbent solution flow rates required in $H_2S$-containing gas deacidizing applications in relation to the reference MDEA absorbent solution.

Example 5: $CO_2$ Absorption Capacity of a N,N,N',N'-(tetramethyl)-1,6-diamino-2,5-hexanediol Formulation for an Acid Gas Treating Method The $CO_2$ absorption capacity performances at 40° C. of an aqueous solution of N,N,N',N'-(tetramethyl)-1,6-diamino-2,5-hexanediol according to the invention, containing 49 wt. % N,N,N',N'-(tetramethyl)-1,6-diamino-2,5-hexanediol, are compared with those of an MDEA aqueous solution containing 47 wt. % MDEA, which is a reference absorbent solution for deacidizing $CO_2$-containing gas.

An absorption test is carried out at 40° C. according to the operating mode described in the previous examples, the acid gas being $CO_2$ instead of $H_2S$.

In the case of deacidizing in natural gas treatment, the $CO_2$ partial pressures encountered in acid gases typically range between 0.1 and 1 bar at a temperature of 40° C. By way of example, in this industrial range, Table 5 below compares the $CO_2$ loadings obtained at 40° C. for various $CO_2$ partial pressures between the 47 wt. % MDEA absorbent solution and the 49 wt. % N,N,N',N'-(tetramethyl)-1,6-diamino-2,5-hexanediol absorbent solution.

TABLE 5

| | 49 wt. % N,N,N',N'-(tetramethyl)-1,6-diamino-2,5-hexanediol aqueous solution at 40° C. | | 47 wt. % MDEA aqueous solution at 40° C. | |
|---|---|---|---|---|
| $CO_2$ partial pressure (bar) | $CO_2$ loading (mol/mol amine) | $CO_2$ loading (mol/kg) | $CO_2$ loading (mol/mol amine) | $CO_2$ loading (mol/kg) |
| 0.10 | 0.88 | 2.12 | 0.22 | 0.88 |
| 1.00 | 1.65 | 3.95 | 0.69 | 2.74 |

At 40° C., whatever the $CO_2$ partial pressure, the absorption capacity of the N,N,N',N'-(tetramethyl)-1,6-diamino-2,5-hexanediol aqueous solution according to the invention is higher than that of the MDEA solution. At a $CO_2$ partial pressure of 0.10 bar, the difference between the $CO_2$ loadings of the two absorbent solutions is 1.24 mol/kg with an absorption capacity for the N,N,N',N'-(tetramethyl)-1,6-diamino-2,5-hexanediol absorbent solution increased by 141% in relation to the reference MDEA absorbent solution. At a $CO_2$ partial pressure of 1 bar, the $CO_2$ loading increase for the N,N,N',N'-(tetramethyl)-1,6-diamino-2,5-hexanediol absorbent solution still is 44% in relation to the reference MDEA absorbent solution. It can thus be observed that the 49 wt. % N,N,N',N'-(tetramethyl)-1,6-diamino-2,5-hexanediol aqueous solution has a higher $CO_2$ absorption capacity than the reference 47 wt. % MDEA aqueous solution at 40° C., in the $CO_2$ partial pressure range between 0.1 and 1 bar corresponding to a partial pressure range representative of usual industrial conditions.

It thus appears that this exemplified molecule according to the invention allows to reduce the absorbent solution flow rates required in $CO_2$-containing gas deacidizing applications compared to the reference MDEA absorbent solution.

Example 6: $CO_2$ Absorption Capacity of a N,N,N',N'-(tetramethyl)-1,8-diamino-2,7-octanediol Formulation for an Acid Gas Treating Method The $CO_2$ absorption capacity performances at 40° C. of an aqueous solution of N,N,N',N'-(tetramethyl)-1,8-diamino-2,7-octanediol according to the invention containing 47 wt. % of N,N,N',N'-(tetramethyl)-1,8-diamino-2,7-octanediol are compared with those of an MDEA aqueous solution containing 47 wt. % MDEA, which is a reference absorbent solution for deacidizing $CO_2$-containing gas.

An absorption test is carried out at 40° C. according to the operating mode described in the previous examples, the acid gas being $CO_2$.

In the case of natural gas treatment deacidizing, the $CO_2$ partial pressures encountered in acid gases typically range between 0.1 and 1 bar, at a temperature of 40° C. By way of example, in this industrial range, Table 6 hereafter compares the $CO_2$ loadings obtained at 40° C. for various $CO_2$ partial pressures between the 47 wt. % MDEA absorbent solution and the 47 wt. % N,N,N',N'-(tetramethyl)-1,8-diamino-2,7-octanediol absorbent solution.

TABLE 6

| | 47 wt. % N,N,N',N'-(tetramethyl)-1,8-diamino-2,7-octanediol aqueous solution at 40° C. | | 47 wt. % MDEA aqueous solution at 40° C. | |
|---|---|---|---|---|
| $CO_2$ partial pressure (bar) | $CO_2$ loading (mol/mol amine) | $CO_2$ loading (mol/kg) | $CO_2$ loading (mol/mol amine) | $CO_2$ loading (mol/kg) |
| 0.10 | 1.02 | 2.06 | 0.22 | 0.88 |
| 1.00 | 1.82 | 3.68 | 0.69 | 2.74 |

At 40° C., whatever the $CO_2$ partial pressure, the absorption capacity of the N,N,N',N'-(tetramethyl)-1,8-diamino-2,7-octanediol aqueous solution according to the invention is higher than that of the MDEA solution. At a $CO_2$ partial pressure of 0.10 bar, the difference between the $CO_2$ loadings of the two absorbent solutions is 1.18 mol/kg with an absorption capacity for the N,N,N',N'-(tetramethyl)-1,8-diamino-2,7-octanediol absorbent solution increased by 134% in relation to the reference MDEA absorbent solution. At a $CO_2$ partial pressure of 1 bar, the $CO_2$ loading increase for the N,N,N',N'-(tetramethyl)-1,8-diamino-2,7-octanediol absorbent solution still is 34% in relation to the reference MDEA absorbent solution. It can thus be observed that the 47 wt. % N,N,N',N'-(tetramethyl)-1,8-diamino-2,7-octanediol aqueous solution has a higher $CO_2$ absorption capacity than the reference 47 wt. % MDEA aqueous solution at 40° C., in the $CO_2$ partial pressure range between 0.1 and 1 bar corresponding to a partial pressure range representative of usual industrial conditions.

It therefore appears that this exemplified molecule according to the invention allows to reduce the absorbent solution flow rates required in $CO_2$-containing gas deacidizing applications in relation to the reference MDEA absorbent solution.

Example 7: Capture Capacity of N,N,N',N'-(tetramethyl)-1,6-diamino-2,5-hexanediol and N,N,N',N'-(tetramethyl)-1,8-diamino-2,7-octanediol aqueous Solutions. Application to Post-Combustion Fumes Treatment The $CO_2$ capture capacity performances of the N,N,N',N'-(tetramethyl)-1,6-diamino-2,5-hexanediol and N, N, N',N'-(tetramethyl)-1,8-diamino-2,7-octanediol according to the invention are notably compared with those of a 30 wt. % MonoEthanolAmine (MEA) aqueous solution which is a reference solvent in capture applications for $CO_2$ contained in post-combustion fumes. An absorption test is first carried out on aqueous amine solutions according to the operating mode described above.

By way of example, Table 7 compares the loadings (α=nb of mol acid gas/nb of mol amine) obtained at 40° C. for various $CO_2$ partial pressures between a 49 wt. % N,N,N',N'-(tetramethyl)-1,6-diamino-2,5-hexanediol aqueous solution according to the invention, a 47 wt. % N,N,N',N'-(tetramethyl)-1,8-diamino-2,7-octanediol aqueous solution according to the invention and a 30 wt. % MonoEthanolAmine aqueous solution for a post-combustion $CO_2$ capture application.

To switch from one loading quantity obtained in the laboratory to a quantity characteristic of the method, some calculations are necessary and explained below for the intended application.

In the case of a post-combustion $CO_2$ capture application, the $CO_2$ partial pressures in the effluent to be treated are typically 0.1 bar with a temperature of 40° C., and 90% of the acid gas is to be abated. The cyclic capacity $\Delta\alpha PC$ expressed in mol of $CO_2$ per kg of solvent is calculated, considering that the solvent reaches a loading in the absorption column bottom corresponding to an equilibrium partial pressure at 40° C. equal to 50% of the partial pressure in the effluent to be treated, i.e. $\alpha PPCO_2 = 0.05$ bar, and needs at least to be regenerated to a loading corresponding to an equilibrium partial pressure equal to 50% of the pressure in the column top conditions, i.e. to $\alpha PPCO_2 = 0.005$ bar, to achieve 90% $CO_2$ abatement.

$$\Delta\alpha_{PC} = (\alpha_{PPCO2-0.005bar} - \alpha_{PPCO2-0.005bar}) \cdot [A] \cdot 10/M$$

where [A] is the amine concentration expressed in wt. %, M the molar mass of the amine in g/mol, and $\alpha_{PPCO2=0.005bar}$ and $\alpha_{PPCO2=0.005bar}$ are the loadings (mol $CO_2$/mol amine) of the solvent at equilibrium with a $CO_2$ partial pressure of 0.05 bar and 0.005 bar respectively.

The reaction enthalpy can be obtained by calculation from several $CO_2$ absorption isotherms by applying Van't Hoff's law.

TABLE 7

| | | | Loading α = $n_{CO2}/n_{amine}$ | | $\Delta\alpha_{PC}$ | |
| --- | --- | --- | --- | --- | --- | --- |
| Generic name | Concentration | T (° C.) | $P_{PCO2}$ = 0.05 bar | $P_{PCO2}$ = 0.005 bar | (mol$_{CO2}$/kg Solvent) | ΔH (kJ/mol$_{CO2}$) |
| MEA | 30 wt. % | 40 | 0.50 | 0.41 | 0.47 | 92 |
| N,N,N',N'-(tetramethyl)-1,6-diamino-2,5-hexanediol (according to the invention) | 49 wt. % | 40 | 0.62 | 0.18 | 1.07 | 74 |
| N,N,N',N'-(tetramethyl)-1,8-diamino-2,7-octanediol (according to the invention) | 47 wt. % | 40 | 0.70 | 0.19 | 1.02 | 73 |

For a post-combustion fumes capture application where the $CO_2$ partial pressure in the effluent to be treated is 0.1 bar, this example illustrates the higher cyclic capacity obtained with 49 wt. % N,N,N',N'-(tetramethyl)-1,6-diamino-2,5-hexanediol and 47 wt. % N,N,N',N'-(tetramethyl)-1,8-diamino-2,7-octanediol absorbent solutions according to the invention, allowing to reach a 90% abatement ratio at the absorber outlet. In this application where the energy associated with the regeneration of the solution is critical, it can be noted that the amine according to the invention allows to obtain a much better compromise than MEA in terms of cyclic capacity and reaction enthalpy.

The invention claimed is:

1. A method of removing acid compounds contained in a gaseous effluent, comprising carrying out an acid compound absorption stage by contacting the gaseous effluent with an absorbent solution comprising water and at least one nitrogen compound belonging to the family of tertiary diamines meeting general formula (I) as follows:

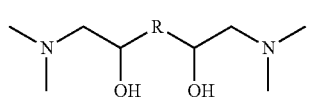

(I)

wherein R is an alkanediyl radical —$(CH_2)n$- with n=2, 3, 4, 5 or 6.

2. A method as claimed in claim 1, wherein the absorbent solution comprises between 5 wt. % and 95 wt. % of said at least one nitrogen compound, and between 5 wt. % and 95 wt. % of water.

3. A method as claimed in claim 1, wherein the absorbent solution additionally comprises between 5 wt. % and 95 wt. % of at least one additional amine, said additional amine being either a tertiary amine or a secondary amine having two secondary carbons at nitrogen alpha position or at least one tertiary carbon at nitrogen alpha position.

4. A method as claimed in claim 3, wherein said additional amine is a tertiary amine selected from among the group made up of:
- N-methyldiethanolamine,
- triethanolamine,
- diethylmonoethanolamine,
- dimethylmonoethanolamine, and
- ethyldiethanolamine.

5. A method as claimed in claim 1, wherein the absorbent solution also comprises a non-zero amount less than 30 wt. % of at least one additional amine.

6. A method as claimed in claim 5, wherein said at least one additional amine is selected from among the group made up of:
- monoethanolamine,
- diethanolamine,
- N-butylethanolamine,
- aminoethylethanolamine,
- diglycolamine,
- piperazine,
- 1-methylpiperazine,
- 2-methylpiperazine,
- homopiperazine,
- N-(2-hydroxyethyl)piperazine,
- N-(2-aminoethyl)piperazine,
- morpholine,
- 3-(methylamino)propylamine,
- 1,6-hexanediamine,
- N,N-dimethyl-1,6-hexanediamine,
- N,N'-dimethyl-1,6-hexanediamine,
- N-methyl-1,6-hexane-diamine, and
- N,N',N'-trimethyl-1,6-hexanediamine.

7. A method as claimed in claim 1, wherein the absorbent solution furthermore comprises at least one physical solvent selected from the group made up of methanol, ethanol, 2-ethoxyethanol, triethylene glycoldimethylether, tetra-ethylene glycoldimethylether, pentaethylene glycoldimethylether, hexaethylene glycoldimethylether, heptaethylene glycol-dimethylether, octaethylene glycol-dimethylether, diethylene glycol butoxyacetate, glycerol triacetate, sulfolane, N-methylpyrrolidone, N-methylmorphlin-3-one, N,N-dimethylformamide, N-formyl-morpholine, N,N-dimethyl-imidazolidin-2-one, N-methylimidazole, ethylene glycol, diethylene glycol, triethylene glycol, thiodiglycol and tributyl phosphate.

8. A method as claimed in claim 1, wherein the gaseous effluent is selected from among natural gas, syngases, combustion fumes, refinery gas, acid gas from an amine plant, Claus tail gas, biomass fermentation gas, cement plant gas and incinerator fumes.

9. A method as claimed in claim 1, implemented for selectively removing the $H_2S$ over the $CO_2$ from a gaseous effluent comprising $H_2S$ and $CO_2$.

10. A method as claimed in claim 1, wherein the absorbent solution comprises between 10 wt. % and 90 wt. % of said at least one nitrogen compound, and between 10 wt. % and 90 wt. % of water.

11. A method as claimed in claim 1, wherein, in general formula (I), n is equal to 2, the at least one nitrogen compound comprising a diamine named, named N,N,N',N'-(tetramethyl)-1,6-diamino-2,5-hexanediol and meeting the formula as follows:

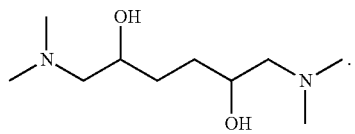

12. A method as claimed in claim 1, wherein, in general formula (I), n is equal to 4, the at least one nitrogen compound comprising a diamine named, named N,N,N',N'-(tetramethyl)-1,8-diamino-2,7-octanediol and meeting the formula as follows:

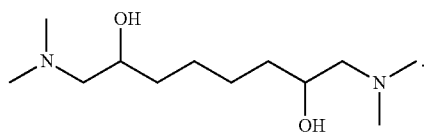

13. A method of removing acid compounds contained in a gaseous effluent wherein an acid compound absorption stage is carried out by contacting the gaseous effluent with an absorbent solution comprising water and at least one nitrogen compound obtained by a synthesis method comprising the following reactions:
- a first reaction of epoxidation of an alpha-omega-diene to achieve epoxidation of each one of the alkene functions of the alpha-omega-diene to oxirane functions so as to produce a diepoxyalkane,
- a second reaction of addition of two moles of dimethylamine and one molecule of the diepoxyalkane so as to produce a nitrogen compound belonging to the family of tertiary diamines meeting general formula (I) as follows:

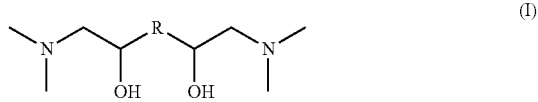

(I)

wherein R is an alkanediyl radical —$(CH_2)n$- with n=2, 3, 4, 5 or 6.

* * * * *